(12) United States Patent
De Vries et al.

(10) Patent No.: US 9,616,025 B2
(45) Date of Patent: Apr. 11, 2017

(54) COMPRESSED TABLET CONTAINING Δ9-TETRAHYDROCANNABINOL, METHOD FOR ITS MANUFACTURE AND USE OF SUCH TABLET IN ORAL TREATMENT

(71) Applicant: Echo Pharmaceuticals B.V., Weesp (NL)

(72) Inventors: Jan Albert De Vries, Zelhem (NL); Maria Vanesa Fernandez Cid, Haarlem (NL); Ana Maria Heredia Lopez, Amsterdam (NL); Cristina Maria Eiroa Martinez, Amsterdam (NL)

(73) Assignee: Echo Pharmaceuticals B.V., Weesp (NL)

( * ) Notice: Subject to any disclaimer, the term of this patent is extended or adjusted under 35 U.S.C. 154(b) by 0 days.

(21) Appl. No.: 15/032,925

(22) PCT Filed: Oct. 29, 2014

(86) PCT No.: PCT/NL2014/050746
§ 371 (c)(1),
(2) Date: Apr. 28, 2016

(87) PCT Pub. No.: WO2015/065180
PCT Pub. Date: May 7, 2015

(65) Prior Publication Data
US 2016/0256395 A1 Sep. 8, 2016

(30) Foreign Application Priority Data
Oct. 29, 2013 (EP) .................................... 13190577

(51) Int. Cl.
*A61K 9/20* (2006.01)
*A61K 31/352* (2006.01)
*A61K 9/14* (2006.01)

(52) U.S. Cl.
CPC .......... *A61K 9/2018* (2013.01); *A61K 9/2009* (2013.01); *A61K 9/2013* (2013.01); *A61K 9/2077* (2013.01); *A61K 9/2095* (2013.01); *A61K 31/352* (2013.01); *A61K 9/145* (2013.01); *A61K 9/2054* (2013.01)

(58) Field of Classification Search
None
See application file for complete search history.

(56) References Cited

U.S. PATENT DOCUMENTS

2002/0015730 A1   2/2002  Hoffmann
2003/0021752 A1   1/2003  Whittle
2006/0076536 A1   4/2006  Barsheid
2010/0008985 A1   1/2010  Pellikaan
2010/0034888 A1*  2/2010  Pellikaan ............. A61K 9/1617
                                                        424/489
2011/0038958 A1   2/2011  Kikuchi et al.

FOREIGN PATENT DOCUMENTS

WO   WO 02/064109 A2    8/2002
WO   WO 2006/063109 A2  6/2006
WO   WO 2006/133941 A2  12/2006
WO   WO 2008/024490 A2  2/2008
WO   WO 2008/033023 A2  3/2008
WO   WO 2008/033024 A2  3/2008
WO   WO 2009/020666 A2  2/2009
WO   WO 2009/087351 A1  7/2009
WO   WO 2012/033478 A1  3/2012

OTHER PUBLICATIONS

Munjal et al. "Polymeric Systems for Amorphous delta9-Tetrahydrocannabinol Produced by a Hot-Melt Method. Part II: Effect of Oxidation Mechanisms and Chemical Interactions on Stability", J Pharm Sci. Nov. 2006, vol. 95, No. 11, pp. 2473-2485.
Ohlsson et al., "Plasma delta-9-tetrahydrocannabinol concentrations and clinical effects after oral and intravenous administration and smoking",Clin. Pharmacol. Ther., Sep. 1980, vol. 28, pp. 409-416.
Ohlsson et al., "Single dose kinetics of deuterium labelled delta-1-tetrahydrocannabinol in heavy and light cannabis users" Biomedical Mass Spectrometry, 1982, vol. 9, No. 1, pp. 6-10.
Leweke et al., "Cannabidiol enhances anandamide signaling and alleviates psychotic symptoms of schizophrenia", Translational Psychiatry, 2012, vol. 2, pp. 1-7.
Poortman-Van Der Meer et al., "A contribution to the improvement of accuracy in the quantitation of THC", Forensic Science International, vol. 101, pp. 1-8.

(Continued)

*Primary Examiner* — Susan Tran
(74) *Attorney, Agent, or Firm* — Foley & Lardner LLP; Sunit Talapatra

(57) ABSTRACT

The present invention relates to compressed tablets for peroral delivery of the cannabinoid Δ9-tetrahydrocannabinol (THC). More particularly, the invention provides a compressed tablet having a tablet weight of 25-1000 mg, said tablet being composed of: compressed tablet containing delta 9-tetrahydrocannabinol, method for its manufacture and use of such tablet in oral treatment •30-90 wt % of a granulate; •10-70 wt % of lactose; and •0-30 wt % of other tablet excipients; wherein the granulate contains: a.2-5 wt % of Δ9-tetrahydrocannabinol; b.2-20 wt % of sucrose fatty acid mono-ester; c.50-96 wt % of lactose; d.0.05-0.6 wt % of antioxidant; and e.0-25 wt % of other granulate excipients. The compressed tablets according to the invention can conveniently be used in the treatment of spasticity and pain caused by multiple sclerosis, neurophatic pain, chronic pain, behavioral disturbance by Alzheimer's disease, stroke, spinal cord injury, peripheral neuropathy, neurogenic pain, nociceptive pain and nausea. The invention further provides a method for the manufacture of the compressed tablets.

14 Claims, No Drawings

(56) References Cited

OTHER PUBLICATIONS

Zhornitsky et al., "Cannabidiol in humans—the quest for therapeutic targets", Pharmaceuticals, 2012, vol. 5, pp. 529-552.
Zuardi et al., "Cannabidiol monotherapy for treatment-resistant schizophrenia", Journal of Psychopharmacology, 2006, vol. 20, No. 5, pp. 683-686.
Zuardi et al., "Cannabidiol, a Cannabis sativa constituent, as an antipsychotic drug", Brazilian Journal of Medical and Biological Research, 2006, vol. 39, pp. 421-429.
International Search Report issued in International Patent Application No. PCT/NL2014/050746 mailed Jan. 19, 2015.
International Search Report issued in International Patent Application No. PCT/NL2014/050745 mailed Feb. 4, 2015.

\* cited by examiner

COMPRESSED TABLET CONTAINING Δ9-TETRAHYDROCANNABINOL, METHOD FOR ITS MANUFACTURE AND USE OF SUCH TABLET IN ORAL TREATMENT

CROSS-REFERENCE TO RELATED APPLICATIONS

This application is the U.S. National Phase of International Patent Application No. PCT/NL2014/050746, filed Oct. 29, 2014, published on May 7, 2015 as WO 2015/065180 A1, which claims priority to European Patent Application No. 13190577.0, filed Oct. 29, 2013. The contents of which are herein incorporated by reference in their entirety.

TECHNICAL FIELD OF THE INVENTION

The present invention relates to compressed tablets containing a granulate that comprises lactose particles, Δ9-tetrahydrocannabinol and a sucrose fatty acid mono-ester. These compressed tablets are particularly suited for peroral administration and can be conveniently used in oral treatment, notably in the treatment of spasticity and pain caused by multiple sclerosis, neurophatic pain, chronic pain, behavioral disturbance by Alzheimer's disease, stroke, spinal cord injury, peripheral neuropathy, neurogenic pain, nociceptive pain and nausea. The invention also provides a method for the manufacture of the compressed tablets.

BACKGROUND OF THE INVENTION

It has been known since long that different cannabinoids, which are the major active constituents of the plant *Cannabis sativa* (cannabis), have pharmacological activity. Well-known examples of such cannabinoids are Δ9-tetrahydrocannabinol (THC) and cannabidiol (CBD).

THC is known to have mild to moderate analgesic effects and can for example be used to alleviate neuropathic pain and spasticity in patients suffering from multiple sclerosis (MS). Other known effects of THC include relaxation, alteration of visual, auditory, and olfactory senses, and appetite stimulation. However, THC is also known to be a psychomimetic component which has been shown to elevate levels of anxiety and psychotic symptoms in healthy individuals.

Bioavailability of pharmaceutical substances taken perorally depends, first of all, on the extent to which the pharmaceutically active substance is absorbed from the intestinal environment across the intestinal mucosa. Lipophilic pharmaceutical substances such as THC are generally poorly absorbed from the intestinal environment, inter alia because of their poor solubility and/or dispersibility in water.

Bioavailability of a pharmaceutical substance taken perorally furthermore depends on the susceptibility of the substance to the so-called first pass effect. Substances absorbed from the intestine, before being distributed throughout the body, have to pass the liver first where they may be metabolized immediately. THC is generally assumed to be rather susceptible to first-pass metabolization.

THC oral absorption is slow and unpredictable, with peak concentrations occurring 1-5 hours post dose. Plasma THC maximum concentrations of 4.4-11.0 μg/L can be achieved after a 20 mg dose of oral THC (Ohlsson et al., *Plasma delta-9-tetrahydrocannabinol concentrations and clinical effects after oral and intravenous administration and smoking*. Clin Pharmacol Ther 1980; 28: 409-16). THC bioavailability is approximately 6% when orally administered, compared to up to 27% when inhaled (Ohlsson et al., *Single dose kinetics of deuterium labelled delta-1-tetrahydrocannabinol in heavy and light cannabis users*. Biomed Environ Mass Spectrom 1982; 9: 6-10).

In view of THC's low oral bioavailability, over the years considerable effort has been put into the development of pharmaceutical delivery systems for alternative routes of administration, such as buccal, sublingual, pulmonal, nasal and rectal administration.

It is also well established that THC is a highly unstable drug. Hence, another important aspect for the formulation of THC dosage forms is to overcome the stability problem. THC is particularly sensitive to oxidation. Presence of cannabinol (CBN), the thermo-oxidative degradation product of THC, in the material is indicative of THC degradation by oxidation. Munjal et al. (*Polymeric Systems for Amorphous Δ9-Tetrahydrocannabinol Produced by a Hot-Melt Method. Part II: Effect of Oxidation Mechanisms and Chemical Interactions on Stability*, J Pharm Sci. 2006 November; 95(11): 2473-2485) describe the outcome of investigations that aimed to elucidate the mechanism for the oxidative degradation of THC in polymer matrix systems prepared by a hot-melt fabrication procedure, and to study the potential for controlling these mechanisms to reduce the degradation of THC in solid dosage formulations.

THC-containing dosage units for oral administration have been described in some patent publications.

WO 95/025504 describes a pharmaceutical preparation comprising a stable emulsion of a pharmaceutical agent incorporated into a hydrophobic emulsion of a long chain carboxylic acid, long chain carboxylic acid ester, long chain carboxylic acid alcohol and mixtures thereof in a dosage form suitable for oral delivery.

WO 02/064109 describes a pharmaceutical formulation for use in administration of a lipophilic medicament via a mucosal surface, which formulation comprises at least one lipophilic medicament and at least one self emulsifying agent. Example 6 of the patent application describes the preparation of a tablet for buccal or sublingual administration by dissolving glyceryl monostearate, polysorbate 80, ascorbyl palmitate and α-tocopherol and THC in alcohol, spraying the alcoholic solution onto a powder mix consisting of lactose and soluble starch, evaporating the alcohol, dusting the resulting granulate with talc and compressing to a target tablet weight of 101 mg.

WO 2006/063109 describes a stabilized oral dosage form of a cannabinoid, comprising a mixture of a therapeutically effective amount of a cannabinoid dispersed in an oil-based carrier contained in unit dosage form selected from a hard gelatin capsule, a cellulosic capsule, a starch capsule, and a non-animal based hydrocolloid film-forming composition.

WO 2006/133941 describes a dosage form comprising a therapeutically effective amount of crystalline THC and a pharmaceutically-acceptable carrier, which dosage unit is adapted for oral administration, parenteral administration, transmucosal administration, transdermal administration, or administration by inhalation.

WO 2008/033023 describes a granulate having a volume weighted mean diameter of 1-200 μm and containing:
- at least 0.1 wt. % of a pharmaceutically active substance, such as cannabinoids;
- at least 10 wt. % of emulsifier, such as sucrose fatty acid ester; and
- 0-89.9 wt. % of a water-dispersible saccharide; the combination of the pharmaceutically active substance, the emulsifier and the water-dispersible saccharide together representing at least 60 wt. % of the granulate; wherein the granulate is monophasic or wherein the granulate comprises a dispersed phase containing the pharmaceutically active substance, said dispersed phase having a volume weighted mean diameter of less than 300 nm. Example 8 describes the preparation of a tabletting powder containing 5 g of a microgranulate and 17 g of other components including 5 g of lactose, the microgranulate being composed of tetrahydrocannabinol and sucrose monolaurate (1:15). The tabletting powder is compressed into tablets of 60 mg.

WO 2008/033024 describes dosage units for sublingual, buccal or oral administration of water-insoluble pharmaceutically active substances. Example 1 describes the preparation of a monophasic microgranulate consisting of THC and sucrose monolaurate in a weight ratio of 1:15 using a dry granulation process. Example 3 of this patent application describes the manufacture of a tabletting powder for direct compression using 5 g of the microgranulate obtained from Example 1 and 17 g of other components including 5 g of lactose and the compression to 7 mm tablets with a total weight of 60 mg.

WO 2009/020666 describes a stabilized cannabinoid formulation suitable for oral administration, comprising a cannabinoid in a semi-aqueous solution buffered to a pH of 5 to 10, the solution comprising water and an organic cosolvent to maintain the physical stability of the formulation.

WO 2012/033478 describes an oral dosage form of cannabinoids in a self-emulsifying system operable to avoid hepatic first pass metabolism, said oral dosage form comprising:

1-90 wt % of a pharmacologically active form of cannabinoids;
15-85 wt % of one or more triglycerides;
15-85 wt % of one or more mixed glycerides; and
5-90 wt % of a surfactant which promotes self-emulsification.

It is an object of the invention to provide a dosage unit for peroral administration of THC that combines excellent (oxidative) stability with high and predictable bioavailability.

SUMMARY OF THE INVENTION

The inventors have developed a compressed tablet for peroral delivery that meets this objective. The tablet according to the present invention has a tablet weight of 25-1000 mg and is composed of: 30-90 wt % of a THC-containing granulate, 10-70 wt % of lactose and 0-30 wt % of other tablet excipients. The granulate contains 2-5 wt % of THC, 2-20 wt % of sucrose fatty acid mono-ester, 50-96 wt % of lactose, 0.05-0.6 wt % of antioxidant and 0-25 wt % of other granulate excipients.

The tablets are very stable in that oxidative degradation of THC within the tablet is effectively minimized.

Furthermore, tablets according to the invention show favourable pharmacokinetic and/or pharmacodynamic characteristics. In particular, formulations according to the invention tested in healthy volunteers proved to be well tolerated, resulted in a relatively short time to reach maximum plasma concentrations, suggesting a fast onset of clinical effects, and showed relatively little inter-individual variability (compared to other oral formulations).

The tablets according to the invention can conveniently be used in the treatment of spasticity and pain caused by multiple sclerosis, neuropathic pain, chronic pain, behavioral disturbance by Alzheimer's disease, stroke, spinal cord injury, peripheral neuropathy, neurogenic pain, nociceptive pain and nausea.

The invention further relates to a method of manufacturing a compressed tablet according to the present invention, said method comprising the steps of:

providing a lactose powder having a mass weighted average diameter of 32-250 μm;
combining the lactose powder with a granulation fluid to produce a granulate, said granulation fluid comprising a solution of Δ9-tetrahydrocannabinol, sucrose fatty acid monoester, antioxidant and optionally further granulate excipients in organic solvent;
removing the organic solvent by evaporation to produce a granulate;
mixing the granulate with lactose powder and optionally further tablet excipients to produce a tablet mixture; and
compressing the tablet mixture into a tablet.

DEFINITIONS

The term 'compressed tablet' as used herein refers to a mixture of active substances and excipients, pressed or compacted from a powder form into the solid pharmaceutical dosage form.

The term 'granulate' as used herein refers to a particulate material that consists of discrete particles, referred to as granules.

The term 'granule' refers to a particle that is composed of two or more sub-particles that are held together by physical forces, e.g. by a binding agent.

The term 'granulation' as used herein refers to a process that converts a powder into a granulate. Wet granulation is a granulation method that employs a fluid to convert a powder into a granulate. The fluid is usually sprayed onto the powder while the powder is kept in motion. The fluid acts as a binding agent that 'glues' together the powder particles, thereby forming granules. This fluid is also referred to herein as 'granulation fluid'. It typically contains a solvent which is sufficiently volatile for removal by drying and that is non-toxic.

The term 'oral' or 'peroral' as used herein, unless indicated otherwise, refers to a mode of administration that involves ingestion of the dosage unit.

The term 'mass weighted average diameter' as used herein refers to the average diameter of particulate matter wherein the contribution of the diameter of a single particle to the average is proportional to the mass of that single particle. The mass weighted average diameter of a powder or a granulate may suitably be measured by analytical sieve analysis.

The term 'volume weighted average diameter' as used herein refers an average particle diameter wherein the contribution of the diameter of a single particle to the average is proportional to the volume of that single particle. The relative volume-contribution of a single particle is usually deemed to be proportional to its (diameter)$^3$. The term 'solid dispersion' refers to compositions containing a drug dispersed or dissolved within a solid carrier matrix. Different types of solid dispersions can be distinguished on the basis of the physical form of the drug and the carrier. The drug is either suspended in the carrier as phase-separated crystalline or amorphous particles, or it exists as a homogeneous molecular mixture of (amorphous) drug and carrier. The carrier can exist in amorphous or crystalline form. More information on solid dispersions can be found in Williams et al., Strategies to Address Low Drug Solubility in Discovery and Development, Pharmacological Reviews (2013) 65, 416-445.

DETAILED DESCRIPTION OF THE INVENTION

A first aspect of the invention relates to a compressed tablet having a tablet weight of 25-1000 mg, said tablet being composed of 30-90 wt % of a granulate, 10-70 wt % of lactose and 0-30 wt % of other tablet excipients, wherein the granulate contains 2-5 wt % of THC, 2-20 wt % of sucrose fatty acid mono-ester, 50-96 wt % of lactose, 0.05-0.6 wt % of antioxidant and 0-25 wt % of other granulate excipients.

The compressed tablet of the present invention is composed of (prepared from) at least two particulate components, i.e. granulate, lactose and optionally one or more tablet excipients. Unless indicated otherwise the lactose concentrations mentioned herein refer to either the lactose that together with the granulate represents the bulk of the compressed tablet or the lactose that is contained within the granulate.

The weight of the compressed tablet preferably is within the range of 40-700 mg, more preferably in the range of 50-500 mg and most preferably in the range of 75-250 mg.

The THC-containing granulate typically represents at least 40 wt. %, more preferably at least 45 wt. % and most preferably at least 50 wt. % of the tablet. Preferably, said granulate represents not more than 80 wt. %, especially not more than 74 wt. % of the tablet.

Lactose, other than the lactose contained in the THC-containing granulate, typically represents of at least 20 wt. %, more preferably of at least 24 wt. % and most preferably of at least 26 wt. % of the tablet. Preferably, said lactose represents not more than 60 wt. %, more preferably not more than 50 wt. % and most preferably not more than 45 wt. % of the tablet.

The optional other tablet excipients are typically contained in the tablet in a concentration of not more than 20 wt. %, more preferably in a concentration of not more than 15 wt. % and most preferably in a concentration of not more than 10 wt. %.

THC is preferably contained in the granulate in a concentration of 2.2-4.5 wt. %, especially of 2.4-4 wt. %.

Sucrose fatty acid mono-ester typically represent at least 3 wt. %, more preferably at least 4 wt. % of the granulate. Preferably the concentration of sucrose fatty acid mono-ester in the granulate does not exceed 15 wt. %, more preferably it does not exceed 12 wt. % and most preferably it does not exceed 10 wt. %.

Lactose is typically contained in the THC-containing granulate in a concentration of at least 75 wt. %, more preferably of at least 80 wt. % and most preferably of at least 85 wt. %. The lactose content of the granulate preferably does not exceed 95 wt. %, more preferably it does not exceed 94 wt. % and most preferably it does not exceed 93 wt. %.

The optional other granulate excipients are typically contained in the granulate in a concentration of not more than 20 wt. %, more preferably in a concentration of not more than 10 wt. % and most preferably in a concentration of not more than 5 wt. %. The term 'granulate excipients' as used in the context of the present invention is not to be construed narrowly. Non-limiting examples of excipients that can conveniently be used in the granulate are preservatives, fats, waxes, and further pharmaceutically active substances, such as further cannabinoids or analgesic drugs.

In another preferred embodiment the compressed tablet contains 0.2-20 mg of THC, more preferably 0.5-10 mg of THC. Even more preferably, the tablet contains 0.7-8 mg THC. Most preferably, the compressed tablet contains 1.2-7.5 mg of THC.

In an embodiment of the invention, the compressed tablet contains 0.2-1.2 mg of THC, more preferably 0.5-1 mg of THC, said tablet being composed of 30-40 wt % of the granulate, 60-70 wt % of lactose and 0-10 wt % of other tablet excipients, preferably being composed of 30-35 wt % of the granulate, 65-70 wt % of lactose and 0-5 wt % of other tablet excipients. Preferably the weight of said compressed tablet is within the range of 25-250 mg, preferably within the range of 50-150 mg.

In another embodiment of the invention, the compressed tablet contains 1.2-2.5 mg of THC, more preferably 1.3-2 mg of THC, said tablet being composed of 60-74 wt % of the granulate, 24-40 wt % of lactose and 0-10 wt % of other tablet excipients, preferably being composed of 65-70 wt % of the granulate, 30-35 wt % of lactose and 0-5 wt % of other tablet excipients. Preferably the weight of said compressed tablet is within the range of 25-250 mg, preferably within the range of 50-150 mg.

In yet another embodiment of the invention, the compressed tablet contains 2.5-7.5 mg of THC, more preferably 4-6 mg of THC, said tablet being composed of 60-74 wt % of the granulate, 24-40 wt % of lactose and 0-10 wt % of other tablet excipients, preferably being composed of 65-70 wt % of the granulate, 30-35 wt % of lactose and 0-5 wt % of other excipients. Preferably the weight of said compressed tablet is within the range of 125-500 mg, preferably within the range of 150-350 mg.

In an embodiment of the invention, a compressed tablet is provided as defined herein, with the proviso that it is not a compressed tablet comprising 75 wt % of a granulate, 23.8 wt. % of lactose, 1 wt % of magnesium stearate and 0.2 wt % of silicon dioxide, wherein the granulate contains 3.0 wt % of THC, 6.0 wt % of sucrose monolaurate, 90.7 wt % of lactose and 0.3 wt % of ascorbic acid.

In a preferred embodiment, the granulate is composed of granules, said granules comprising lactose particles that are held together by a solid dispersion containing the THC, antioxidant, sucrose fatty acid mono-ester and optionally other granulate excipients.

The solid dispersion comprising THC and sucrose fatty acid mono-ester is clearly distinguishable from the lactose particles and acts as a 'glue' that holds together the lactose particles within the granules that make up the granulate.

In an even more preferred embodiment, the granulate is composed of granules, said granules comprising lactose particles that are held together by a solid dispersion, wherein the solid dispersion contains a dispersed phase comprising THC. Preferably, this dispersed phase containing THC has a volume weighted average diameter between 2 nm and 1 µm, more preferably of 2-500 nm, most preferably of 2-300 nm. The person skilled in the art is familiar with suitable techniques for determining the volume weighted average diameter of the dispersed particles containing THC. Transmission electron microscopy is an example of a analytical technique that can be used to determine the volume weighted average diameter of the dispersed phase of the solid dispersion.

Typically, the particles of THC are in an amorphous state. The sucrose monolaurate typically is present in the solid dispersion in an amorphous state.

In a preferred embodiment, the granules constituting the granulate has a mass weighted average diameter of 50-1000 μm, more preferably of 90-500 μm and most preferably of 160-355 μm.

In a preferred embodiment the lactose constituting the lactose particles within the granulate is anhydrous lactose (β-lactose) or α-lactose monohydrate. Anhydrous lactose is substantially free of (crystal) water. α-lactose monohydrate is lactose in which the lactose molecule is associated with 1 molecule of water. The water is incorporated in the crystal lattice and forms an integral part of it.

In a preferred embodiment, 70-100 wt % of the lactose within the granulate consists of β-lactose, more preferably 75-100 wt %, even more preferably 80-100 wt %.

In a preferred embodiment, 90-100 wt % of the lactose within the granulate consists of crystalline lactose, more preferably 95-100 wt %, even more preferably 98-100 wt %.

The THC-containing granulate preferably contains 0.1-0.5 wt %, more preferably 0.2-0.4 wt % of antioxidant. The inventors have found that the inclusion of antioxidant significantly improves the stability of the THC within the tablet.

In a preferred embodiment of the invention, the ratio of antioxidant to THC (w/w) is within the range of 1:20-1:5, more preferably 1:15-1:7.5.

Non-limiting examples of antioxidants that can be employed in the granulate include α-tocopherol (vitamin E), ascorbic acid (vitamin C), esters of ascorbic acid, vitamin A, flavanoids, polyphenols, butylated hydroxy anisole, carotenes, ubiquinol (coenzyme Q10), and combinations thereof. In a preferred embodiment the antioxidant is selected from ascorbic acid, esters of ascorbic acid and combinations thereof. Examples of esters of ascorbic acid that may be employed include fat-soluble esters of ascorbic acid with long-chain fatty acids (e.g. ascorbyl palmitate or ascorbyl stearate). Most preferably, the antioxidant employed is ascorbic acid.

Sucrose fatty acid mono-esters are amphiphilic compounds, i.e. they comprise a hydrophilic and a lipophilic part. The balance between their hydrophilicity and lipophilicity can be expressed in the so-called HLB value. According to a particularly preferred embodiment, the sucrose fatty acid mono-ester has an HLB-value of 8-18, more preferably of 11-17 and most preferably of 13-16.

In a preferred embodiment, the fatty acid residue of the sucrose fatty acid mono-ester, is selected from $C_8$-$C_{18}$ fatty acids. In an even more preferred embodiment, the fatty acid residue of the sucrose fatty acid mono-ester is a saturated $C_{10}$-$C_{18}$ fatty acid. In an even more preferred embodiment, the fatty acid residue of the sucrose fatty acid mono-ester is selected from lauric, palmitic or stearic acid. In a most preferred embodiment, the sucrose fatty acid mono-ester is sucrose monolaurate.

Commercially available sucrose fatty acid mono-esters usually contain small amounts of sucrose fatty acid di-esters. The present granulate preferably comprises less than 50 wt % of sucrose fatty acid di-ester by weight of the sucrose fatty acid mono-ester, more preferably less than 10 wt % of sucrose di-esters by weight of the sucrose fatty acid mono-ester.

In a preferred embodiment of the invention, the ratio of THC to sucrose fatty acid mono-ester (w/w) is within the range of 1:4-1:1, most preferably within the range 1:3-1:1.5.

In a preferred embodiment of the invention, the lactose that is combined with the granulate and optional other tablet excipients to form the compressed tablet, is anhydrous lactose (β-lactose) or α-lactose monohydrate, most preferably it is anhydrous lactose. In a preferred embodiment, 70-100 wt % of the lactose consists of β-lactose, more preferably 75-100 wt %, even more preferably 80-100 wt %. Furthermore, in a preferred embodiment, 90-100 wt % of the lactose consists of crystalline lactose, more preferably 95-100 wt %, even more preferably 98-100 wt %.

The compressed tablet according to the invention may in addition to the granulate and the lactose further include other tablet excipients. These further tablet excipients are advantageously chosen from the group consisting of coloring agents, flavoring or taste masking agents, muco-adhesive agents, diluents, binders, lubricants, additional disintegrants other than lactose, stabilizers, surfactants, glidants, plasticizers, preservatives and sweeteners. These tablet excipients may be distributed throughout the tablet or they may be contained in, for instance, an external coating, such as an enteric coating.

Suitable muco-adhesive agents that can be added to the compressed tablets are chosen from the group consisting of carbomers, cellulose derivatives, plant lectin, dextrin, hypromellose, chitosan, polyethylene oxide, alginate and combinations thereof. In a preferred embodiment the compressed tablets comprise 0-3 wt % of muco-adhesive agents.

The additional disintegrants are advantageously chosen from the group consisting of, crospovidone, croscarmellose sodium, sodium starch glycolate, hydroxypropyl cellulose, polacrilin potassium, pregelatinized starch, microcrystalline cellulose and combinations thereof. In a preferred embodiment the compressed tablets comprise up to 20 wt % of additional disintegrants.

The compressed tablets of the present invention may suitably comprise one or more coating layers, e.g. an enteric coating. These coating layers together represent no more than 20 wt % of the tablet.

In order to enable easy removal of the compressed tablets from the moulds, the compressed tablets typically contain 0.1-10 wt % of a lubricant or gliding agent. Preferably, the lubricant or gliding agent is selected from the group consisting of talc, sodium stearyl fumarate, magnesium stearate, calcium stearate, hydrogenated castor oil, hydrogenated soybean oil, polyethylene glycol, starches, anhydrous colloidal silica and combinations thereof. In a preferred embodiment the compressed tablets comprise 0.5-2 wt % of lubricant.

According to a preferred embodiment, the compressed tablets of the present invention comprise a combination of silica and lubricant.

Advantageously, the compressed tablets exhibit a certain level of porosity in order to allow easy water access. Typically, the compressed tablets of the present invention exhibit a porosity of 1-50%, preferably of 2-15%, said porosity being defined as the volume of void space in a compressed tablet divided by the total volume of the compressed tablet, multiplied by 100. Analysis techniques for determining porosity of solid pharmaceutical dosage forms are well known to those skilled in the art.

The compressed tablet of the invention may be contained in a suitable package, preferably a package that is air-tight. In a particularly preferred embodiment, the package is a blister pack comprising a front sheet and a back sheet sealed together to define one or several sealed pockets, each pocket containing a compressed tablet of the invention. The front sheet or back sheet may be shaped or molded to have preformed pockets that can contain a tablet. The front sheet and back sheet furthermore may be the respective parts of a folded single sheet of material. Blister packs may e.g. contain 1, 2, 4, 6, 8, 10, 12, 14, 16, 18 or 20 pockets comprising a compressed tablet. In a particularly preferred embodiment of the invention, the seals between the front sheet and the back sheet are air-tight. Preferably the front sheet and the back sheet comprise or consist of a material that renders the sheet substantially or entirely impermeable to air, humidity and/or gas, preferably a material selected from the group consisting of aluminum, Polyvinyl chloride (PVC), polypropylene (PP), and polyethylene (PE), most preferably aluminum. Hence, in an embodiment of the invention, a blister pack as defined here before is provided, wherein exchange of gaseous substances between the inside of a pocket and the environment surrounding it does not occur.

In a preferred embodiment of the invention, a package as defined herein is provided, wherein the space that is not occupied by the compressed tablets of the invention is filled with an inert gas, especially an inert gas selected from the group consisting of argon, nitrogen and helium, most preferably argon.

Another aspect of the invention relates to a method of manufacturing a compressed tablet granulate as described herein before, said method comprising the steps of:
providing a lactose powder having a mass weighted average diameter of 32-250 µm, preferably of 45-250 µm;
combining the lactose powder with a granulation fluid to produce a granulate, said granulation fluid comprising a solution of THC, sucrose fatty acid mono-ester, antioxidant and optionally further granulate excipients in an organic solvent;
removing the organic solvent by evaporation to obtain the granulate;
mixing the granulate with lactose powder and optionally further tablet excipients to produce a tablet mixture; and
compressing the tablet mixture into a tablet.

In accordance with a preferred embodiment of the present method, the granulation fluid is combined with the lactose powder to produce the granulate by gradually adding the granulation fluid to the lactose powder, whilst agitating the lactose powder. The granulation fluid may suitably be added onto a powder bed which is agitated under the influence of an impeller (e.g. in a high shear granulator, screws (e.g. in a twin screw granulator) or air (e.g. in a fluidized bed granulator). More preferably, the granulate is produced in a high shear granulator.

As is known to those skilled in the art, the rate of adding the granulation fluid to the powder, the ratio of granulation fluid to powder and the degree of agitation of the wet mass all affect the final particle size distribution of the granules. It is within the skills of the expert in the field of pharmaceutical drug formulation to steer at the desired particle size distribution.

Preferably, the amount of granulation fluid employed in the preparation of the granulate is in the range of 5-100% by weight of the lactose powder with which it is combined. Even more preferably, granulation fluid is employed in an amount of 10-50%, most preferably of 20-25% by weight of said lactose powder.

The granulation fluid is typically combined with the lactose powder at a rate of at least 2 ml per kg of lactose powder per minute. Even more preferably the addition rate is in the range of 3-200 ml/kg/min, most preferably in the range of 4-100 ml/kg/min.

In a preferred embodiment, the temperature of the granulation fluid is between 15° C. and 50° C. when it is combined with the lactose powder.

The organic solvent contained in the granulation fluid preferably is $C_1$-$C_3$ alcohol, more preferably a $C_1$-$C_3$ alcohol chosen from the group consisting of methanol, ethanol, n-propanol, isopropyl alcohol and combinations thereof. In a particularly preferred embodiment, the $C_1$-$C_3$ alcohol is ethanol.

Evaporation of the organic solvent can be accomplished by any means known in the art. In a preferred embodiment, vacuum drying is applied to remove the organic solvent. In a more preferred embodiment, the vacuum drying is applied at a temperature of between 20° C. and 70° C., even more preferably at a temperature of between 35° C. and 55° C.

In another preferred embodiment, the granulation fluid is prepared by combining the THC, sugar fatty acid mono ester antioxidant and optionally further granulate excipients, in the (relative) amounts recited here above, in an organic solvent at a combined total level within the range of 0.5-1.5 g per ml of solvent, more preferably within the range of 0.55-1.3 g per ml of solvent, most preferably within the range of 0.6-1.2 g per ml of solvent.

In a preferred embodiment of the invention, the granulation fluid comprises a dispersion or solution in the organic solvent of:
0.1-0.5 g/ml of THC;
0.2-1 g/ml of sugar fatty acid mono-ester;
0.004-0.04 g/ml of antioxidant; and
0-0.4 g/ml of other granulate excipients;
preferably at a combined total level within the range of 0.5-1.5 g per ml of solvent, more preferably within the range of 0.55-1.3 g per ml of solvent, most preferably within the range of 0.6-1.2 g per ml of solvent.

In a preferred embodiment of the invention, the ratio of THC to sucrose fatty acid mono-ester (w/w) in the granulation fluid is within the range of 1:5-1:0.5, more preferably 1:4-1:1, more preferably 1:3-1:1.5.

The compressed tablets of the present inventions are conveniently produced in a tabletting machine. Tablet manufacturing methods by powder compression are generally known to those skilled in the art.

In an embodiment of the invention, a process is provided as defined above, further comprising the step of packaging the compressed tablet, preferably in a package that is air-tight. In a particularly preferred embodiment, the package is a blister pack and the process comprises the steps of:
collecting a predetermined number of compressed tablets;
placing said compressed tablets in between a front sheet and a back sheet;
sealing together the front sheet and the back sheet in a pattern creating one or more discrete pockets, each pocket containing a compressed tablet.

The front sheet or back sheet may be shaped or molded to have preformed pockets that can contain a tablet. The front sheet and back sheet furthermore may be the respective parts of a folded single sheet of material. In accordance with this process a number of e.g. 1, 2, 5, 10, 15 or 20 compressed tablets may be packaged in a single blister pack. In a preferred embodiment of the invention, the seals between the front sheet and back sheet are air-tight. Preferably the front sheet and back sheet comprise or consist of a material that renders it substantially or entirely impermeable to air, humidity and/or gas, preferably a material selected from the group consisting of aluminum, Polyvinyl chloride (PVC), polypropylene (PP), and polyethylene (PE), most preferably aluminum.

In a preferred embodiment of the invention, the process of packaging the compressed tablets as defined above is performed in a space filled with an inert gas, especially an inert gas selected from the group consisting of argon, nitrogen and helium most preferably argon.

Another aspect of the invention relates to compressed tablets comprising THC as defined herein for use in the treatment of spasticity and pain caused by multiple sclerosis, neurophatic pain, chronic pain, behavioral disturbance by Alzheimer's disease, stroke, spinal cord injury, peripheral neuropathy, neurogenic pain, nociceptive pain and nausea, said treatment comprising oral administration of the dosage unit.

In a preferred embodiment, said treatment comprises daily peroral administration of one or more the compressed tablets in a total amount that is equivalent to 0.75-75 mg of THC, more preferably in a total amount that is equivalent to 2.25-45 mg of THC.

In another preferred embodiment the treatment comprises daily peroral administration of 1 to 10 compressed tablets, more preferably 1 to 5, even more preferably 1 to 3. The compressed tablets are conveniently administered at regular time intervals in the range of 4-24 hours, such as one tablet every 4 hours, every 6 hours, every 8 hours, or once a day.

Treatment of the aforementioned disorders in the context of the present invention involves both therapeutic and prophylactic treatments.

The compressed tablets of the present invention are advantageously employed in the treatment of mammals, preferably of humans.

The following examples are meant to further illustrate the invention and some of its preferred embodiments without intending to limit its scope.

EXAMPLES

Example 1

A THC-granulate was prepared via a wet-granulation method. The composition of the THC-granulate is described in Table 1.

TABLE 1 composition THC-granulate

| Component | wt % |
|---|---|
| THC | 3.0 |
| Sucrose monolaurate | 6.0 |
| Ascorbic acid | 0.3 |
| Lactose[1] | 90.7 |

[1]Anhydrous, crystalline lactose (mass weighted average particle size appr. 150 μm)

A granulation fluid containing THC, sucrose monolaurate and ascorbic acid at a combined concentration of 0.7 g/ml was prepared as follows. The required amount of THC was weighed in a beaker. In another beaker, the ascorbic acid (AA) was dissolved in 120 ml of ethanol. The solution was heated to 60° C. and stirred to help the dissolution of AA. Dissolution of AA was completed in approximately 15 minutes. When the AA had been dissolved, the solution was added to the beaker containing the THC. The required amount of sucrose monolaurate (SML) was also added to the beaker containing the THC. The mixture was heated to 45° C. and stirred to help the dissolution. The granulation fluid was stirred during 10 to 15 minutes until all the material was dissolved.

The wet granulation process was performed as follows. Lactose was weighed and transferred to the mixing bowl of a high shear granulator. The system was closed and the heating for the heating jacket of the granulation vessel was turned on (set temperature of 40° C.). Before addition of the granulating fluid, vacuum was applied and nitrogen was pumped into the vessel. Subsequently, the granulating fluid was added by dripping using a peristaltic pump at 9 ml/min while the impeller and the chopper were turning. When the granulating fluid was completely added to the granulation vessel, the drying process was started. Vacuum drying occurs under a stream of nitrogen (200 cc/min). The drying process was completed when the temperature (50° C.) and vacuum remained stable for at least 15 minutes and no liquid was coming from the condenser. After completion of the drying process, the vacuum was released, the nitrogen flow was closed and the granulate was collected and transferred to a sieve. The granulate was sieved through sieves of 2.0 mm, 0.710 mm and 0.355 mm. The final THC-granulate was packed into an aluminum bag. The granulate A had a mass weighted average diameter of 355 μm. The binding component of granulate A consists of a solid dispersion of THC.

Example 2

The THC-granulate obtained in Example 1 was blended with excipients and directly compressed into tablets comprising 0.75, 1.5 or 5 mg THC for peroral administration. The components and weights used for tablet preparation are given in Table 2. Specifications of the compressed tablets are given in Table 3.

TABLE 2 compositions used for the preparation of tablets comprising 0.75, 1.5 or 5 mg THC

| | 0.75 mg THC | | 1.5 mg THC | | 5 mg THC | |
|---|---|---|---|---|---|---|
| Component | wt % | weight [mg] | wt % | weight [mg] | wt % | weight [mg] |
| Granulate A | 33.3 | 24.98 | 66.7 | 50.00 | 66.7 | 166.67 |
| Lactose[1] | 65.5 | 49.13 | 32.1 | 24.10 | 32.1 | 80.33 |
| Magnesium stearate | 1.0 | 0.75 | 1.0 | 0.75 | 1.0 | 2.50 |
| Silicon dioxide, anhydrous | 0.2 | 0.15 | 0.2 | 0.15 | 0.2 | 0.50 |
| Total | 100 | 75 | 100 | 75 | 100 | 250 |

[1]Anhydrous, crystalline lactose, mass weighted average diameter appr. 150 μm

TABLE 3 specification of the compressed tablets

| Parameter | Method | Specification |
|---|---|---|
| Hardness | Ph. Eur. 2.9.8 | ≥20N |
| Diameter | — | 5.9-6.1 mm [75 mg tablets] 8.9-9.1 mm [250 mg tablets] |
| Dissolution | Ph. Eur. 2.9.3 | ≥75% (Q) within 45 minutes |
| Disintegration | Ph. Eur. 2.9.1 | <15 minutes |
| Residual ethanol | Ph Eurr. 2.4.24 | ≤5000 ppm |

Example 3

The rate of dissolution of THC from the compressed tablets described in Example 2 was tested according to European Pharmacopeia (Ph. Eur. 2.9.3) for oral tablets (5 mg THC). The rate of dissolution of pure THC (5 mg) was also measured according to the same method for comparison.

The dissolution medium consisted of a solution of 1 wt % SDS in water. The pH of the medium had been adjusted to pH 7 with diluted HCl. During the experiments, the temperature of the dissolution media was maintained between 36 and 41° C. under stirring.

After dropping the tablets in the dissolution medium, samples were taken at various time intervals with a disposable syringe. The samples were filtered immediately over a syringe filter into a HPLC vial and analyzed by HPLC. The results of the dissolution tests are summarized in Table 4

TABLE 4

| % (w/w) of THC dissolved | | |
|---|---|---|
| Time (in min.) | Tablet | Pure THC |
| 1 | 69.8 | 1.0 |
| 4 | 91.1 | 3.5 |
| 8 | 93.3 | 5.8 |
| 15 | 95.8 | 10.2 |

Example 4

Tablets from example 2 were packaged in aluminum pouches under nitrogen atmosphere. These packaged tablets were stored under different storage conditions.

The following storage conditions were tested:
1 year at 5° C.
1 year at 40° C./75% RH
2 years at −20° C.
2 years at 25° C./60% RH Tablets were found to be stable under all of these storage conditions, i.e. THC content did not decrease by more than 10%.

Example 5

Tablets of the invention were packaged in Alu-Alu monoblisters under a protective atmosphere of Argon. These packaged tablets were found to be stable for at least two years at 25° C./60% RH.

Example 6

THC-granulate was produced with different types of lactose. The general composition of the THC-granulates is described in Table 5.

TABLE 5

| composition THC-granulates | |
|---|---|
| Material | Wt. % |
| Lactose | 88 |
| THC | 4 |
| Sucrose monolaurate | 8 |
| Ascorbic Acid | 0.2 |

A granulation fluid containing THC was prepared as follows. The ascorbic acid (AA) was dissolved in 120 ml of ethanol. The solution was heated to 60° C. and stirred until the total dissolution of AA. The solution was added to a beaker containing the required amount of SML and stirred until the total dissolution of the SML particles. The AA-SML dissolution was transferred to the beaker containing THC. The mixture was heated to 45° C. and stirred to help the dissolution. The granulation fluid was stirred until all the material was dissolved.

This granulation fluid was used to prepare a granulate using anhydrous lactose (Granulate A) and a granulate using lactose monohydrate (Granulate B).

The wet granulation process was performed as follows for the two batches. Lactose was weighed and transferred to the round bottom drying flask. Carefully, part of the granulation fluid was added to the lactose. The system was closed and the heating was turned on (set temperature of 40° C.). The solvent was evaporated while the granulate was mixed under continuous vacuum. When evaporation was finished the other part of the granulation fluid was added and the same procedure of drying was applied. The drying process was completed when a pressure of <30 mbar was reached.

The obtained granulate was sieved through sieves of 0.355 mm. The final THC-granulate was packed into an aluminum bag.

Example 7

The THC-granulates obtained in Example 6 were blended with excipients and directly compressed into tablets comprising THC for peroral administration. Different types of lactose were used as tabletting excipients.

The composition of the tabletting blends are shown in Table 6.

TABLE 6

| composition of tablets (parts by weight) | | | |
|---|---|---|---|
|  | 1 | 2 | 3 |
| Granulate A | 50 |  |  |
| Granulate B |  | 50 | 50 |
| Anhydrous lactose | 50 | 50 |  |
| Lactose monohydrate |  |  | 50 |
| Magnesium stearate | 1 | 1 | 1 |
| Silidium dioxide, anhydrous | 0.2 | 0.2 | 0.2 |

A stability study was performed with the different tablets during 3 months at 5° C. and room temperature (RT). Tablets 1 produced with THC-granulate containing anhydrous lactose and anhydrous lactose as excipient showed the best stability; (THC content of ≥90% after 3 months at RT). Tablets 2 created with THC-granulate containing lactose monohydrate and anhydrous lactose as excipient had less favorable stability (THC content of 85%-90% after 3 months at RT). The least favorable results in stability were obtained with tablets 3 containing lactose monohydrate in the granulate and as the tabletting excipient (around 75% THC content after 3 months at RT).

Comparative Example A

Tablets were prepared as in Example 2, except that the sucrose fatty ester (SML) was substituted by glyceryl monostearate (GMS). Dissolution tests as described in example 3 were performed with these tablets and the tablets described in Example 2. The results of these experiments are summarized in Table 7.

TABLE 7

| % (w/w) of THC dissolved | | |
|---|---|---|
| Time (in min.) | SML tablet | GMS tablet |
| 1 | 9.7 | 1.4 |
| 4 | 44.3 | 7.8 |

TABLE 7-continued

| | % (w/w) of THC dissolved | |
|---|---|---|
| Time (in min.) | SML tablet | GMS tablet |
| 8 | 74.8 | 16.4 |
| 15 | 89.7 | 35.1 |
| 30 | 91.4 | 69.9 |
| 45 | 94.9 | 89.1 |

Example 8

Oral tablets containing 1.5 mg and 5.0 mg of pure, natural THC as described in Example 2 were used for dose-ranging studies in nine healthy volunteers.

The study was a randomized, double-blind, placebo controlled, three-way dose-escalation trial. This study was designed to investigate two administration routes and three different oral doses.

Tablets containing 5.0 mg or 1.5 mg or matching placebos were used for the administration of 6.5 mg or 8.0 mg THC or placebo respectively.

Plasma concentrations of THC and its active metabolite 11-OH-THC, were analyzed using liquid chromatography/mass spectrometry/mass spectrometry (LC/MS/MS) according to good laboratory practice procedures.

Descriptive statistics were applied to calculate peak plasma concentration ($C_{max}$), time to peak plasma concentration ($t_{max}$), apparent terminal half-life ($t_{1/2}$), and area under the curve from t=0 to infinity ($AUC_{(0,\infty)}$).

The results of these experiments are summarized in Table 8.

TABLE 8

| Pharmacokinetic parameters - Means with coefficient of variation (%) | | |
|---|---|---|
| | 6.5 mg oral (n = 9) | 8.0 mg oral (n = 9) |
| THC | | |
| $C_{max}$ (ng ml$^{-1}$) | 4.43 (42) | 4.69 (62) |
| $t_{max}$ (min) | 39.3 (20) | 43.6 (26) |
| $AUC_{(0,\infty)}$ (ng ml$^{-1}$ min) | 286.6 (36) | 377.2 (46) |
| $t_{1/2}$ (min) | 80.0 (22) | 78.8 (21) |
| 11-OH-THC | | |
| $C_{max}$ (ng ml$^{-1}$) | 5.94 (44) | 6.10 (53) |
| $t_{max}$ (min) | 46.1 (28) | 78.4 (63) |
| $AUC_{(0,\infty)}$ (ng ml$^{-1}$ min) | 848.7 (42) | 1087.3 (50) |
| $t_{1/2}$ (min) | 318.7 (54) | 314.1 (58) |

This data shows that for the tablets tested maximum THC plasma concentration was reached in 39-56 minutes. This outcome compares favourably with reported $t_{max}$-values in previous studies using oral THC (60-240 min), nabilone (120-240 min), or oral-mucosal THC+CBD (Sativex, 198-240 min).

The THC tablets tested also had a shorter time to maximal concentration of the active metabolite 11-OHTHC (46-84 min) compared with what has been published for dronabinol (120-204 min) and Sativex (216-234 min).

The invention claimed is:

1. A compressed tablet having a weight of 25-1000 mg, comprising:
   (a) 30-90 wt % of a granulate;
   (b) 10-70 wt % of lactose; and
   (c) 0-30 wt % of other tablet excipients,
wherein the granulate comprises:
   (i) 2-5 wt % of Δ9-tetrahydrocannabinol (THC);
   (ii) 2-20 wt % of sucrose fatty acid mono-ester;
   (iii) 50-96 wt % of lactose;
   (iv) 0.05-0.6 wt % of antioxidant; and
   (v) 0-25 wt % of other granulate excipients; and
   wherein the granulate comprises granules comprising lactose particles held together by a solid dispersion comprising Δ9-tetrahydrocannabinol, antioxidant, sucrose fatty acid mono-ester and optionally other granulate excipients.

2. The compressed tablet according to claim 1, wherein the granulate comprises 2.2-4.5 wt % of THC and 3-15 wt % of sucrose fatty acid mono-ester.

3. The compressed tablet according to claim 1, comprising 0.5-10 mg of THC.

4. The compressed tablet according to claim 1, wherein the solid dispersion comprises a dispersed phase comprising Δ9-tetrahydrocannabinol, and having a volume weighted average diameter between 2 nm and 1 μm.

5. The compressed tablet according to claim 1, wherein the lactose contained within the granulate is anhydrous lactose.

6. The compressed tablet according to claim 1, wherein the granulate comprises granules that have a mass weighted average diameter of 50-1000 μm.

7. The compressed tablet according to claim 1, wherein the antioxidant is ascorbic acid.

8. The compressed tablet according to claim 1, wherein the fatty acid residue of the sucrose fatty acid mono-ester is a saturated $C_{10}$-$C_{18}$ fatty acid.

9. The compressed tablet according to claim 1, which does not comprise 75 wt % of a granulate, 23.8 wt. % of lactose, 1 wt % of magnesium stearate and 0.2 wt % of silicon dioxide, wherein the granulate contains 3.0 wt % of Δ9-tetrahydrocannabinol, 6 wt % of sucrose monolaurate, 90.7 wt % of lactose and 0.3 wt % of ascorbic acid.

10. A method of manufacturing a compressed tablet according to claim 1, comprising:
   (a) providing a lactose powder having a mass weighted average diameter of 32-250 μm;
   (b) combining the lactose powder with a granulation fluid comprising a solution of Δ9-tetrahydrocannabinol, sucrose fatty acid monoester, antioxidant and optionally further granulate excipients in organic solvent;
   (c) removing the organic solvent by evaporation to produce a granulate;
   (d) mixing the granulate with lactose powder and optionally further tablet excipients to produce a tablet mixture; and
   (e) compressing the tablet mixture into a tablet.

11. The method according to claim 10, wherein the granulation fluid comprises a dispersion or solution in an organic solvent of:
   (a) 0.1-0.5 g/ml of Δ9-tetrahydrocannabinol;
   (b) 0.2-1 g/ml of sugar fatty acid mono-ester;
   (c) 0.004-0.04 g/ml of antioxidant; and
   (d) 0-0.4 g/ml of other granulate excipients;
at a combined total level within the range of 0.5-1.5 g per ml of solvent.

12. The method according to claim 10, wherein the organic solvent is $C_1$-$C_3$ alcohol.

13. A method of treating spasticity or pain caused by multiple sclerosis, neurophatic pain, chronic pain, behavioral disturbance by Alzheimer's disease, stroke, spinal cord injury, peripheral neuropathy, neurogenic pain, nociceptive pain and nausea, the method comprising perorally administering a compressed tablet according to claim 1.

14. The method according to claim 13, comprising daily administration of one or more of the tablets in a total amount that is equivalent to 0.75-75 mg of Δ9-tetrahydrocannabinol.

* * * * *